United States Patent [19]
Coates

[11] Patent Number: 4,681,581
[45] Date of Patent: Jul. 21, 1987

[54] ADJUSTABLE SIZE DIAPER AND FOLDING METHOD THEREFOR

[76] Inventor: Fredrica V. Coates, 1608 Dublin Rd., Charlottesville, Va. 22903

[21] Appl. No.: 558,273

[22] Filed: Dec. 5, 1983

[51] Int. Cl.⁴ .............................................. A61F 13/16
[52] U.S. Cl. .................................... 604/391; 604/394; 604/400
[58] Field of Search ........ 604/385, 391, 392, 389–390, 604/400, 394, 393

[56] References Cited

U.S. PATENT DOCUMENTS

| | | |
|---|---|---|
| 2,290,110 | 7/1942 | McGraw . |
| 2,703,577 | 3/1955 | May . |
| 2,739,594 | 3/1956 | Baten ..................................... 604/392 |
| 2,832,346 | 4/1958 | Morstad . |
| 2,910,982 | 11/1959 | Woodward . |
| 3,081,772 | 3/1963 | Brooks et al. . |
| 3,089,494 | 5/1963 | Schwartz . |
| 3,131,693 | 5/1964 | Gray et al. . |
| 3,141,461 | 7/1964 | Farris . |
| 3,150,664 | 9/1964 | Noel . |
| 3,359,980 | 12/1967 | Rosenblatt . |
| 3,369,545 | 2/1968 | Wanberg . |
| 3,395,707 | 8/1968 | Whalen et al. . |
| 3,554,195 | 1/1971 | Murdoch . |
| 3,618,608 | 11/1971 | Brink . |
| 3,653,381 | 4/1972 | Warnken . |
| 3,955,575 | 5/1976 | Okuda . |
| 4,051,854 | 10/1977 | Aaron . |
| 4,402,690 | 9/1983 | Redfern . |

Primary Examiner—C. Fred Rosenbaum
Assistant Examiner—Sherri E. Vinyard
Attorney, Agent, or Firm—Lowe Price LeBlanc Becker & Shur

[57] ABSTRACT

Various embodiments of a diaper adapter to fit adults as well as infants up to three years of age comprise absorbent material having an inner surface adapted to contact the user and an outer surface. Tabs carrying a filamentary type attachment material extend from the corners at one end of the diaper. At the opposite end, an elongated bar of a complementary filamentary type attachment material is on the inner surface of the diaper and parallel to the end. The bar, termed a "frontal movable fastening bar", is front folded onto the outer surface of the diaper and moved longitudinally toward the middle of the diaper until the proper length for the user is established. Side portions of the diaper are optionally folded to the proper width and the tabs are pulled around the waist and coupled to the bar.

29 Claims, 47 Drawing Figures

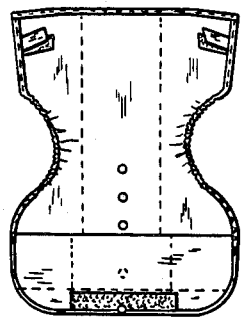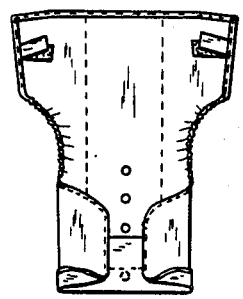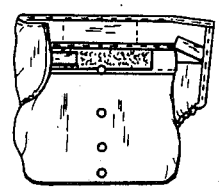
Fig. 3A  Fig. 3B  Fig. 3C
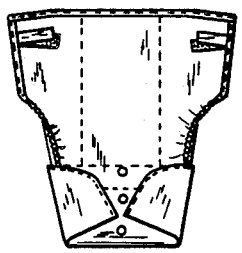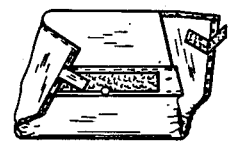
Fig. 3D  Fig. 3E
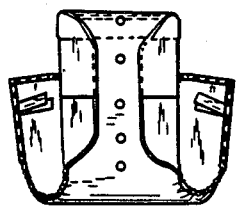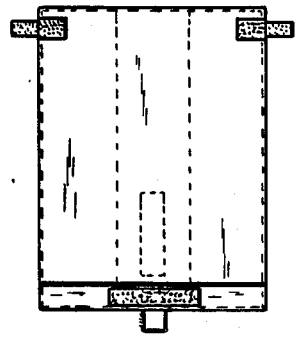
Fig. 3F  Fig. 4

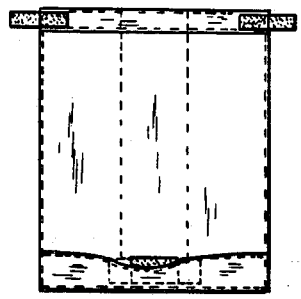
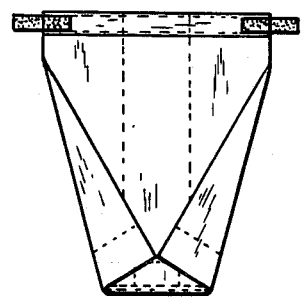
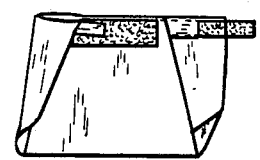
Fig. 5A  Fig. 5B  Fig. 5C
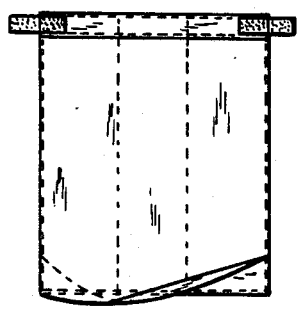
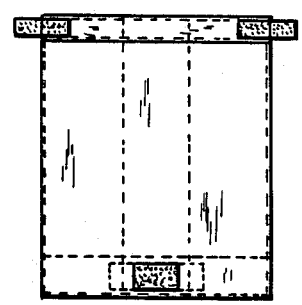
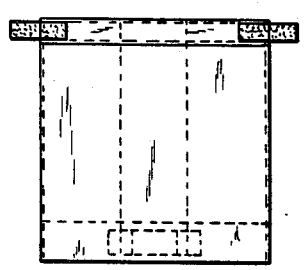
Fig. 5D  Fig. 5E  Fig. 5F
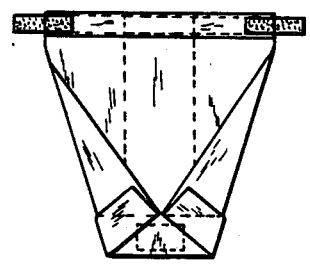
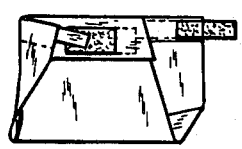
Fig. 5G  Fig. 5H

ADJUSTABLE SIZE DIAPER AND FOLDING METHOD THEREFOR

CROSS REFERENCE TO RELATED APPLICATIONS

This application is related to my co-pending applications Ser. No. 315,049, filed Oct. 26, 1981, and Ser. No. 375,231, filed May 15, 1982.

BACKGROUND ART

Diapers to be worn by growing babies and by adults must be comfortable while permitting free movement, and must be absorbent and economical, while avoiding irritation of the skin. Commonly, a diaper is formed of a rectangular piece of cloth that is secured to the baby or adult using pins. Because pins are inconvenient and since there has been in the past a movement toward disposability, diapers made of moisture absorbent paper and adhesive strips have been developed as a substitute for cloth diapers.

Although convenient, paper diapers tend to be expensive on a per-use basis, the adhesive strips tend to tear from the diaper and the fit is awkward. Furthermore, some babies and adults are allergic to paper diapers and, worst of all, there have been infant deaths by choking, caused by ingestion of the paper.

In response, there has been a recent return toward cloth diapers, with fasteners not of adhesive but rather of filamentary hook and loop material. In my co-pending application Ser. No. 315,049, filed Oct. 26, 1981, I have described a cloth diaper having filamentary type hook and loop fasteners that is adapted to be folded and secured, to accommodate infant growth. My later co-pending application Ser. No. 375,231, filed May 5, 1982, is directed toward, among other things, laundering of the diaper; self-closing attachment tabs protect the hook and loop filamentary material from lint during wash. Although satisfactory, the diapers of my applications tend to be costly to manufacture, since the hook and loop fasteners are provided on the diaper in several different places. The cost of hook and loop filamentary material is high, and manufacture of my prior diapers is labor intensive since the several pieces of filamentary material have to be separately stitched to the diaper. Furthermore, adjustment of the size of the diaper to the size of the wearer, although effective over a wide range of body sizes, requires several folding steps. Further, the filamentary fastening strips, being distributed on the outer surface of the diaper, limit the size adjustability of the diaper, and backfolding of the diaper toward the wearer for length adjustment, with material being bunched against the skin, is cumbersome.

DISCLOSURE OF INVENTION

An object of the present invention is to provide a new and improved fabric diaper that is adjustable in size and securely fits the user.

Another object is to provide a new and improved fabric diaper using hook and loop filamentary fasteners, which is economical to manufacture and requires a minimum amount of filamentary fastener material.

A further object is to provide a new and improved diaper that is continuously adjustable in size along a large range of sizes to fit newborn infants and toddlers up to at least three years of age.

A still further object is to provide a new and improved fabric diaper having filamentary type fasteners that are not adversely affected by laundering.

In accordance with one aspect of the invention, a diaper is formed of an absorbent material having an inner surface adapted to contact the skin of the wearer and an outer surface. Attachment tabs formed of a first type of filamentary material extend from opposite sides at one end of the diaper. At the opposite end of the diaper, on the inner surface, is an elongated bar of a complementary filamentary type attachment material. The bar is parallel to the opposite end of the diaper and is adapted to be coupled to the attachment tabs when worn. The diaper is applied to the wearer by first positioning the inner surface of the diaper against the wearer's skin, front folding the diaper at the bar onto the outer surface of the diaper, and moving the bar downward along the outer surface of the diaper for shortening to the proper length. Side portions of the diaper are optionally front folded prior to front folding of the bar or are back folded following front folding of the bar, to establish the proper width of the diaper. The attachment tabs are pulled around the waist of the wearer, to be coupled to the frontal bar to secure the diaper to the wearer.

In accordance with another aspect of the invention, a portion of the diaper adjacent the lower edge of the frontal bar may be stitched (VELCRO loop fabric form a tuck) to cause the bar to tend to front fold onto the outer surface of the diaper. This assists in front folding of the diaper since the frontal bar tends to "point" to the direction of movement of the bar for diaper shortening.

As another aspect of the invention, the attachment tabs are formed of a first strip of filamentary type attachment material and a second strip of a complementary filamentary type material attached to one end of the first strip, with both strips attached to an edge of the diaper. The second strip functions as a lint cover for the first strip, and the two strips tend to self-close during laundering. Preferably, the two strips are inserted in the edge of the diaper and stitched under a folded edge seam, to reduce the number of steps required to manufacture the diaper. To further reduce the number of manufacturing steps, the frontal bar may also be sewn on the edge seam at the upper end of the diaper, enabling the entire diaper to be manufactured using a single circumferential stitch.

As still a further aspect of the invention, complementary filamentary type attachment strips may be sewn back-to-back to opposite surfaces of the diaper. In one size, the outer strip is coupled to the attachment tabs. The diaper is shortened by front folding the upper end of the diaper to expose the inner strip for coupling to the attachment tab. An end cuff is foldable to extend over the inner or outer surface of the diaper, to insulate the skin from either of the two back-to-back strips.

An additional object of the invention is to provide a diaper that, although usable on babies, is adjustable in width by an amount sufficient to enable the diaper to accommodate substantial variations in adult waistlines. Thus, in accordance with a still further aspect of the invention, receiver loops are positioned at one end of the diaper. A belt positioning strip longitudinally extends along a central portion of the outer surface of the diaper, and a belt adapted to contact the positioning strip extends through the loops. Using filamentary attachment material, the belt is releasably secured selectively to different longitudinal portions of the positioning strip, depending upon desired diaper length.

Still other objects and advantages of the present invention will become readily apparent to those skilled in this art from the following detailed description, wherein I have shown and described only the preferred embodiments of the invention, simply by way of illustration of the best modes contemplated by me of carrying out my invention. As will be realized, the invention is capable of other and different embodiments, and its several details are capable of modification in various, obvious respects, all without departing from the invention. Accordingly, the drawings and description are to be regarded as illustrative in nature, and not as restrictive.

BRIEF DESCRIPTION OF THE DRAWING

FIGS. 3A-3F illustrate another, modified embodiment, together with a folding method;

FIG. 4 is a view of a further embodiment of the invention;

FIGS. 5A-5H show still a further diaper embodiment, together with a folding method;

BEST MODE FOR CARRYING OUT THE INVENTION

Figure 1A:
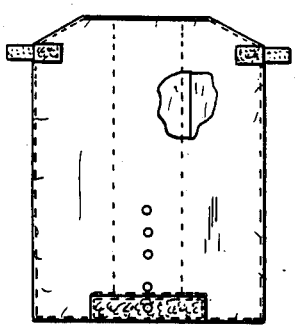
FIGS. 1A-1F illustrate a diaper in accordance with a first embodiment of the invention, as well as a method for folding the diaper.
Figure 1B:
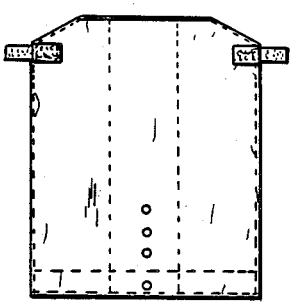
Figure 1C:
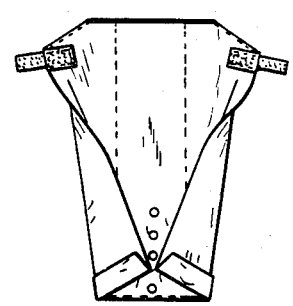

Referring to FIGS. 1A-1G, a diaper 20, in accordance with one embodiment of the invention, comprises a piece of water absorbent fabric 22 having an inner surface 26 (see FIG. 1A) adapted to contact the skin of a wearer and an outer surface 24 (see FIG. 1B). At one end of the fabric 22 and extending outwardly from opposite sides of the fabric are a pair of attachment tabs 28 formed of a filamentary type attachment material. The filamentary type attachment material may be Velcro type or Aplix type hook and loop filamentary material; other suitable types, however, can also be used. At the opposite end of the fabric 22 on inner surface 26 is an elongated bar 30 of a complementary filamentary type material adapted to couple with attachment tabs 28. For example, if attachment tabs 28 are formed of hook type filamentary attachment material, bar 30 is formed of loop type filamentary material. The bar 30 has a length that ranges from approximately ½ to approximately ¾ the width of the diaper 22. This range of lengths is preferred to provide a bar 30 that is long enough to accommodate infants or adults having a relatively large range of waistlines, while freeing opposite side portions of the fabric 22 to be folded inwardly as shown in FIG. 1C to reduce diaper width.

The bar 30 is located immediately adjacent one end of diaper fabric 22. Immediately above the bar 30 is a stitch 32, forming a tuck. The tuck causes the bar 30 to tend to fold over onto the outer surface 24 of diaper fabric 22, as shown in FIG. 1B. The purpose of the tuck 32, discussed in detail below, is to assist the user (mother, attendant, etc.) to roll the bar 30 downwardly along the outer surface of the fabric, at the front of the wearer, to shorten the diaper. The length of the diaper is then fixed by coupling a male snap 34 on bar 30 to an appropriate one of several corresponding female snaps 36 distributed along the center of the diaper fabric 22. The bar 30 is thereafter coupled to attachment tabs 28 to secure the diaper to the wearer.

The snaps 34, 36 are optional. The snaps 34, 36 can be replaced by filamentary attachment material 38, 40 (FIGS. 4 and 8), or can be eliminated to reduce cost.

The diaper fabric 22 is separated into three sections by a pair of longitudinal seams 42 and 44. The inner section 46 is preferably padded for additional absorbency, whereas the outer sections 48, 50 are preferably unpadded to enable the sides of the diaper fabric 22 to be folded inwardly, as shown in FIG. 1C, to reduce the width of the diaper for a proper fit.

Figure 1D:
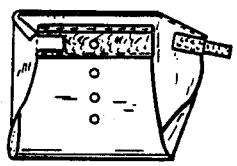
Figure 1E:
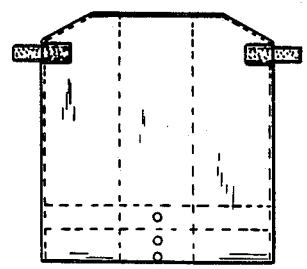
Figure 1F:
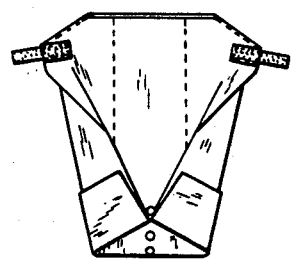
Figure 1G:

The diaper is applied to a wearer by making a combination of folds, using the frontal movable fastening bar 30, in the manner shown in FIGS. 1B-1D for a relatively long diaper length and in FIGS. 1E-1G to establish a diaper having a relatively short length.

In FIGS. 1B-1D, the diaper is initially unfolded and the inner surface 26 of the diaper fabric 22 is positioned against the skin of the wearer. The frontal bar 30 is first folded onto the outer surface 24 of the diaper fabric (into the plane of the drawing in FIG. 1B onto the opposite surface of the fabric), and the frontal bar is moved to a longitudinal position corresponding to the desired length of the diaper. In FIG. 1C, the bar 30 is snapped into the first snap 36 to form a diaper of maximum length. The side panels 48, 50 of diaper fabric 22 are now folded inwardly, as shown in FIG. 1C, to establish the proper width of the diaper 20. The front folded bar 30 is exposed in FIG. 1C; note that only the frontal bar, and not the trailing fabric, is front folded to form the maximum length diaper. The tabs 28 are finally coupled to suitable places on frontal bar 30, as shown in FIG. 1D to secure the diaper to the wearer. FIGS. 1E-1G correspond respectively to FIGS. 1B-1D, except that in FIGS. 1E-1G, the frontal bar 30 is front folded and snapped into the lowest one of the snaps 36, to form a diaper having an effective length that is substantially shorter than that of the diaper folded in accordance with FIGS. 1B-1D. It is noted particularly that in FIG. 1F, the length of the front folded portion 51 corresponds to the width of bar 30 as well as to the length of the trailing fabric. The shortened diaper, following coupling of tabs 28 to bar 30, is shown in FIG. 1G.

Adjacent tabs 28 on the diaper fabric 22 are strips 52 of filamentary type attachment material complementary to the material of tabs 28 and identical to the material of frontal bar 30. The purpose of strips 52 is to protect tabs 28 from the accumulation of lint during washing. Prior to washing the diaper, the tabs 28 are manually folded onto the strips 52, and with the strips and tabs coupled together as shown in FIG. 1G, the filamentary hooks are of tabs 28 are insulated from lint and other debris. Self-closing strips are described infra (FIG. 3A).

Figure 2A:
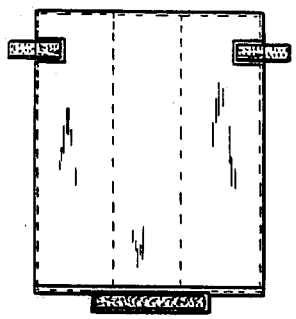
FIGS. 2A-2G illustrate a second diaper embodiment, together with a folding method.
Figure 2B:
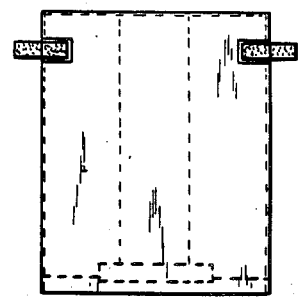

The diaper and folding method shown in FIGS. 2A-2G are similar to those of FIGS. 1A-1G, with a difference being in the manner by which frontal bar 30 is attached to diaper fabric 22. Whereas in FIG. 1A all four edges of frontal bar 30 are stitched to the fabric 22, and the bar is "inboard" to the fabric, in FIG. 2A only one edge of bar 30 is stitched to tuck 32 formed at one edge of the fabric. The bar 30 thus has a tendency to fold around the diaper to the outer surface 24, as shown in FIG. 2B. An optional thumb tab 54 at the free end thus "points" in the direction of frontal folding to adjust the length of the diaper as shown in FIG. 2B.

Figure 2C:
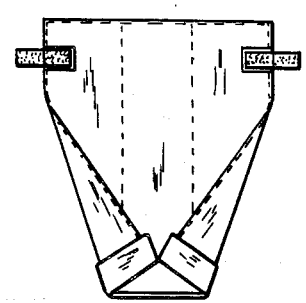
Figure 2D:
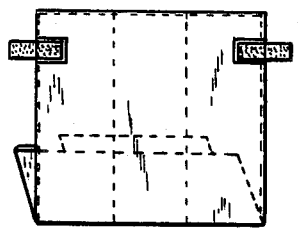
Figure 2E:
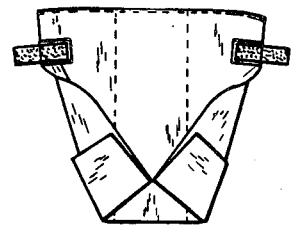
Figure 2F:
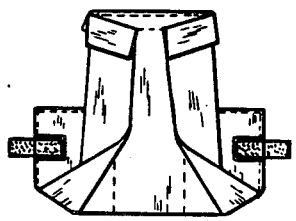
Figure 2G:

In FIGS. 2B-2C, a short frontal fold of bar 30 is made. As shown in FIG. 2C, side portions are optionally front folded and tabs 28 are finally secured to the bar (not shown). In FIG. 2D, a larger portion of the diaper at bar 30 is front folded prior to front folding of opposite side portions, shown in FIG. 2E, to reduce the width of the diaper. FIGS. 2F and 2G show an "accordion" fold whereby a portion of the diaper shown in FIG. 2F raised above tabs 28 is doubled down into the position shown in FIG. 2G to establish a diaper having a minimum length. The attachment tabs 28 are now coupled to bar 30 to secure the diaper to the wearer.

FIGS. 3A-3F illustrate an embodiment of the diaper 41 that is hourglass shaped, rather than rectangular, to more closely fit the contour of an infant. Referring to FIG. 3A, a piece of water impervious material 56 is sewn onto to the inner surface of moisture absorbent fabric 58; a layer of moisture absorbent is also positioned on the entire outer surface of the fabric 58, to form a diaper-water-barrier jacket combination. Longitudinal stitches 42, 44 establish three discrete sections of the diaper 41, with the middle section between stitches 42 and 44 being preferably padded. A pocket in fabric 56 formed between stitch lines 42 and 44 receives an optional additional diaper (not shown) for additional absorbency.

The diaper 41 is manufactured by first positioning the bar 30 on the diaper as shown in FIG. 3A, and making a tuck 32 at the upper edge of the bar 30, with the tuck extending slightly beyond the opposite ends of the bar, as shown. Attachment tabs 28 and complementary strips 52 are positioned at the opposite end of the diaper, facing inward as shown in FIG. 3A, with corresponding ends of the tabs and strips at the outer edge of the diaper. This orientation causes end tab 28 adjacent strip 52 to tend to self-close to each other. The edge of the diaper 41 is now folded over onto the tabs 28 and strips 52, and a single continuous stitch is made along the edge, as shown in FIG. 3A, securing the strips and tabs while reinforcing the edge of the diaper. Elastic material 60 is optionally positioned within the fold at the curved portions of the diaper, to ensure a tight fit of the diaper around the legs. Following formation of the single continuous edge stitch, the frontal bar 30 is secured onto the fold. In other words, whereas the strips and tabs 28, 52 are under the edge fold, the bar 30 is sewn onto the fold. Bias material (not shown) may alternatively be stitched to the diaper edge to replace the edge fold.

In use, side flaps formed by panels 56, 58 are front folded inwardly (FIG. 3B), and frontal bar 30 is folded onto the outer surface of the diaper and secured at the upper snap to form a maximum length diaper. The tabs 28 are now coupled to bar 30, as shown in FIG. 3C.

In FIG. 3D, the frontal bar 30 is coupled to the innermost snap 36 to form a diaper having a short effective length, the side flaps are folded inward, and attachment tabs are coupled to the bar 30, as shown in FIG. 3E, to secure the diaper to the wearer. FIG. 3F shows the inner surface of the diaper prior to frontal folding of bar 30 to form a diaper of a proper effective length.

FIG. 4 is similar to FIG. 1A, with strips of filamentary attachment material replacing the snaps of FIG. 1A. The filamentary attachment material provides an infinite adjustment of effective length of the diaper. A portion 64 of filamentary material complementary to material 62, protects tab 62 from lint. Prior to laundering, tab 62 is manually folded onto portion 64 to provide insulation in the same manner as provided by lint cover 52 in FIG. 1A.

Referring to FIGS. 5A-5H, in accordance with another embodiment of the invention the inner surface 26 of a diaper 51 has a first block 66 of filamentary type attachment material. On the outer surface of the diaper fabric, back to back with block 66, is a second, longer block of filamentary type material 68. At the end of the diaper adjacent blocks 66 and 68 is a cuff 70 having a length great enough to cover either block 66 or 68, depending upon the surface of the diaper over which the cuff is oriented. In the position shown in FIG. 5A, the cuff 70 is oriented over block 66, insulating the block from the skin of the user. In FIG. 5D, the cuff is being flipped to the opposite side of the diaper fabric, covering block 72. With the larger block 68 exposed, the diaper is capable of being folded into a large effective size; with the smaller block 66 exposed, the diaper is folded into a smaller effective size.

More particularly, with the cuff 70 folded over block 66 in FIG. 5A, side portions of the diaper are initially folded inward to establish the proper width, as shown in FIG. 5B, and the diaper is folded upward, as shown in FIG. 5C, to enable tabs 28 to couple to block 68, establishing a diaper having a relatively large effective size.

With the cuff 70 now folded under the fabric as shown in FIG. 5D, to cover the larger block 68 and expose the smaller block 66, the side panels of the diaper are folded inward as shown in FIG. 5G to establish a proper width. The diaper is now folded upward to the proper length, and the surface of the diaper fabric carrying block 66 is folded down, as shown in FIG. 5H to expose the block. Tabs 28 are now coupled to block 66 to form a diaper having a relatively small effective width. In other words, in FIG. 5H the front portion of the diaper is "doubled over" to reduce the length of the diaper. In either case, the skin of the wearer is insulated from the two blocks 66, 72 of filamentary attachment material.

Figure 6A:
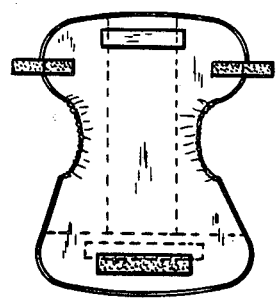
FIGS. 6A-6G illustrate a diaper jacket cover of plastic water-barrier material, together with a folding method, in accordance with another aspect of the invention.
Figure 6B:
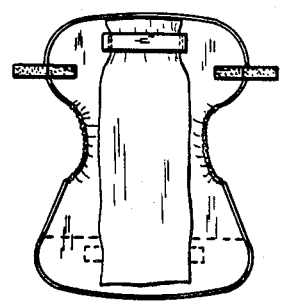

FIGS. 6A-6G are directed toward another embodiment wherein the principles of the invention are adapted to a diaper cover 71. The diaper cover 71 is formed of a water impervious layer within an outer skin of fabric, with the edge reinforced by a bias material 72, and an elastic material 74 at the legs. At one end of the inner surface 73 of the diaper cover, a strip of material 76 secures a diaper to the cover, as shown in FIG. 6B. At the opposite end of the cover, a first block of filamentary type material 78 is stitched. A second block 80 of filamentary material having a length slightly greater than the length of the first block, is on the outer surface 75 of the cover 71.

Figure 6C:
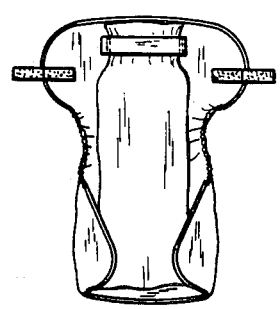
Figure 6D:
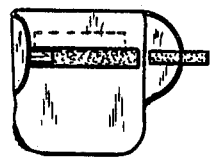

To establish a diaper cover of a first effective size, the side portions of the cover are folded inwardly as shown in FIG. 6C. The diaper cover is then folded upward, orienting strips 80 to attachment tabs 28, as shown in FIG. 6D. The tabs 28 are now coupled to strip 80, securing the cover to the wearer.

Figure 6E:
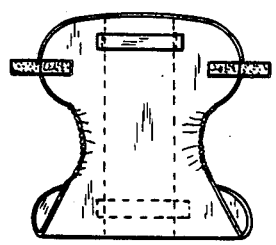
Figure 6F:
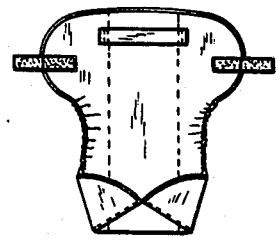
Figure 6G:
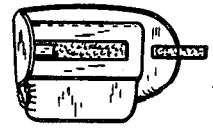

In FIG. 6E, the lower portion of the diaper cover is first front folded onto the outer surface of the diaper cover, as shown in FIG. 6E. The sides of the cover are folded inward to the proper width, as shown in FIG. 6F, and the cover is folded upward to align strip 78 with attachment tabs 20. The tabs 28 and strips 78 are now coupled together to secure the diaper cover, having a length shorter than the length shown in FIG. 6D, to the wearer.

Figure 7:
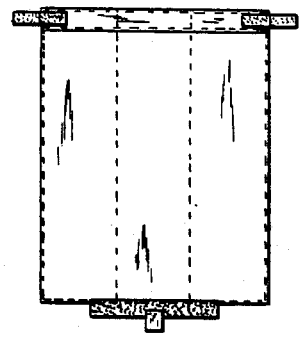
FIG. 7 illustrates a diaper that is a modification of the diaper shown in FIGS. 2A-2G.

The embodiment in FIG. 7 is similar to the embodiment of FIG. 2A. Strips 28 in FIG. 7 are located on a backband 80 in FIG. 7 for reinforcement.

Figure 8:
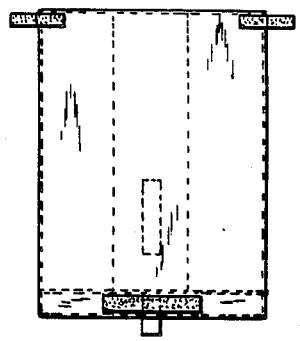
FIGS. 8 and 8A illustrate a diaper embodiment that is similar to the embodiment of FIG. 4.
Figure 8A:
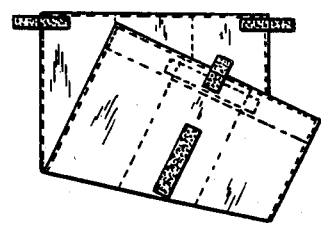

FIG. 8A is similar to FIG. 4, with tabs 28 and covers 52 extending outwardly from opposite sides of the diaper, as contrasted with FIG. 4, wherein strips 52 are "inboard". The tab-cover strip configuration in FIG. 8 provides self-closure of the tabs 28 and strips 52 during laundering. I have found, however, that to optimize closure of the tabs 28 and strips 52, the width of the strips must be greater than the widths of the tabs, and the lengths of the tabs must be no greater than twice the widths of the tabs.

Figure 9:
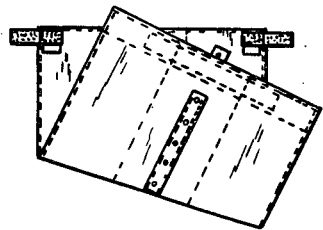
FIG. 9 illustrates a diaper embodiment that is generally similar to the embodiment shown in FIGS. 1A-1G.

FIG. 9 is similar to FIG. 1A, with female snaps 36 provided on a fastener strip 82 to be coupled selectively to male snap 84. The embodiment of FIG. 9 is easier to manufacture than the embodiment of FIG. 1A since the fastener strip 82 eliminates multiple stitching of individual snaps 36 onto the diaper fabric.

Figure 10:
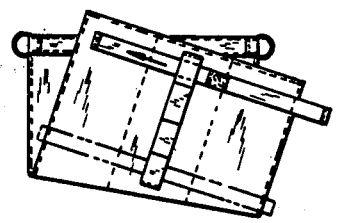
FIGS. 10 and 10A illustrate a diaper in accordance with another aspect of the invention, having a waist belt, particularly adapted for adults.
Figure 10A:
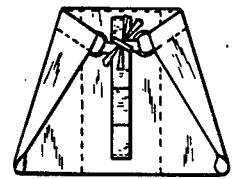

FIGS. 10 and 10A are directed toward a diaper embodiment that is particularly useful as an adult diaper, wherein there is a substantial variation in waistlines among users. Diaper 90 has an inner surface 92 adapted to contact the skin of the wearer and an outer surface 94. On opposite sides of the diaper at one end thereof there are a pair of D-rings 96. The D-rings 96 are preferably retained within a reinforcement belt 98 that in turn is stitched to the diaper fabric.

On the outer surface 94 of the diaper 90 is a central band 100 stitched to the diaper fabric at several points to establish a number of loops, as shown.

A belt 102 extends through the strip 100, at a loop that depends upon the effective size of the diaper desired. The belt shown in solid lines in FIG. 10 extends through the outer loop of strip 100, to establish a diaper of a large effective size. A diaper of a small effective size is established by passing the belt through the inner loop, as shown in phantom in FIG. 10, with the portion of diaper above the belt being tucked against the skin of the wearer.

The diaper is secured to the wearer by passing the ends of the belt 102 through D-rings 96, preferably at the rear of the wearer. The belt is now tightened around the waist of the wearer and tied, as shown in FIG. 10A.

Of particular importance is that, to prevent the belt 102 from slipping or becoming lost when the diaper and belt are stored, the inner surface of the belt 102 is provided with a strip of filamentary attachment material 104 which couples with complementary filament type attachment material on the inner surface of strip 100. Thus, strip 100 is preferably formed of a strip of filamentary type attachment material with the filamentary material facing the diaper and adapted to couple to belt strip 104.

FIGS. 11A-11E are similar to FIGS. 10 and 10A. The outer surface 106 of diaper 108 is provided with a strip of filamentary type attachment material, partitioned to form loops. Extending through one of the loops is a belt 116 formed of filamentary attachment material complementary to the attachment type material of strip 110. The strip 110 and belt 116 are oriented with their respective filamentary type attachment materials facing each other. The purpose of the filamentary materials is to cause the belt 116 to be retained within the desired loop of strip 110 when worn or when stored.

The outer surface 106 of the diaper 108 also contains, at the opposite end of the diaper, a pair of D-rings 112 on opposite ends of a fabric strip 114.

Figure 11A:
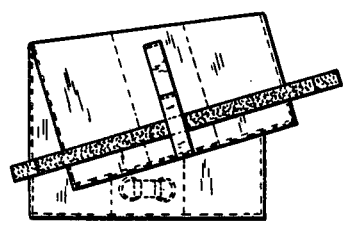
FIGS. 11A-11E illustrate a diaper embodiment similar to the embodiment shown in FIGS. 10 and 10A.
Figure 11B:
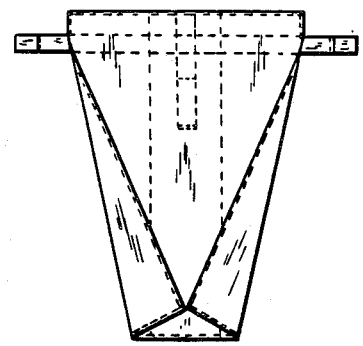
Figure 11C:
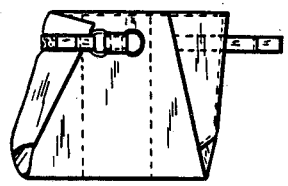
Figure 11D:
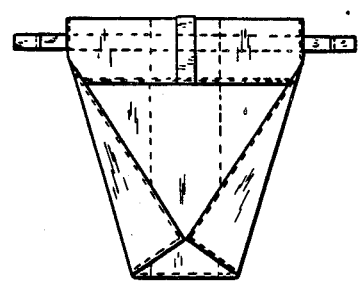
Figure 11E:
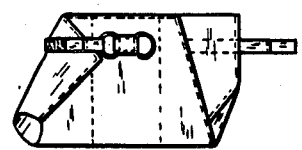

Referring to FIG. 11B, the diaper is oriented with the strip 110 at the back side of the wearer. Side portions of the diaper are folded inward to the proper width, and the diaper is folded upward, through the crotch, with the D-rings 112 over the back side of the wearer, as shown in FIG. 11C. With the D-rings 112 oriented at the same height as the belt 116, the belt is brought through the D-rings. Ends of the belt are formed with complementary filamentary type material to enable the ends of the belt to fold back through the rings and couple to themselves, as shown in FIG. 11E.

In this disclosure, there are shown and described only the preferred embodiments of the invention but, as aforementioned, it is to be understood that the invention is capable of use in various other combinations and environments and is capable of changes or modifications within the scope of the inventive concept as expressed herein.

I claim:

1. A baby or adult diaper that is adjustable in size, comprising:
   an absorbent material having an inner surface adapted to contact the skin of the user when worn, and an outer surface;
   attachment tabs formed of a first type of filamentary attachment material extending from opposite sides of said diaper material at one end of the diaper; and
   an elongated bar of a complementary type of filamentary attachment material located centrally between said sides on the inner surface of said diaper material adjacent and parallel to an opposite end of the diaper, said bar having a length from about one half to about three fourths the full width of the diaper material;
   a portion of the diaper material carrying the bar being adapted to be front folded onto the outer surface of the diaper material and positioned longitudinally on the diaper material to establish a proper diaper length for the user,
   a central, longitudinally extending first fastener means on the outer surface of the diaper material,
   a second fastener means on the outer surface of the diaper material opposite the bar and adapted to be coupled to said longitudinal fastener means,
   said attachment tabs being adapted to be coupled to said bar to secure the diaper to the user.

2. The diaper of claim 1, wherein the outer surface diaper material adjacent one edge of said bar is stitched against the bar to form a tuck causing the bar to tend to front fold onto the outer surface of said diaper material.

3. The diaper of claim 1, including a central, longitudinal fastening means on the outer surface of the diaper material, and complementary fastening means extending longitudinally from said bar for securing said bar to a predetermined position on said diaper material.

4. The diaper of claim 3, wherein said longitudinal fastening means and said complementary fastening means comprise filamentary attachment material.

5. The diaper of claim 3, wherein said longitudinal fastening means and said complementary fastening means comprise snaps.

6. The diaper of claim 1, wherein only one edge of said bar is stitched to said diaper material, the bar extending outwardly from said diaper material.

7. The diaper of claim 1, wherein said attachment tabs are each formed of a first strip of filamentary attachment material and a second strip of complementary filamentary attachment material, corresponding ends of said first and second strips being secured to each other and to said diaper material, said second strip functioning as a lint cover for said first strip.

8. The diaper of claim 7, wherein said second strip has a width that is greater than the width of said first strip.

9. The diaper of claim 7, wherein said first strip has a length-to-width ratio less than or equal to 2.

10. The diaper of claim 7, wherein said first and second strips extend inwardly, outer edges thereof being inserted within a folded side edge of said diaper material to reinforce attachment of the strips to the diaper.

11. The diaper of claim 10, wherein portions of the perimeter of the diaper material are back folded and sewn over one end of each of the first and second strips to secure and reinforce said strips to the diaper.

12. The diaper of claim 10, including a strip of bias material on at least portions of the perimter of the diaper material for securing and reinforcing the first and second strips to the diaper.

13. The diaper of claim 12, further including an elastic band within said folded edge to cause the diaper to tend to hug the user's legs.

14. The diaper of claim 1, wherein the inner surface of said diaper includes means for retaining an absorbent material thereon.

15. A baby or adult diaper that is adjustable in size, comprising:
   an absorbent material having an inner surface adapted to contact the skin of a user when worn, and an outer surface;
   attachment tabs formed of a first type of filamentary attachment material extending from opposite sides of said diaper material at one end of the diaper;
   a first strip of complementary type attachment material on the inner surface of the diaper material, centrally located and spaced from the opposite end of the diaper;
   a second strip of said complementary type filamentary attachment material on the outer surface of the diaper material, back-to-back with the first strip; and
   a cuff of said diaper material formed at said opposite end of said diaper and having a length sufficient to cover either one of said first and second strips, said cuff being alternatively foldable on the inner surface of the diaper material to cover said first strip or on the outer surface to cover the second strip.

16. In a baby or adult diaper that is adjustable in size and is formed of an absorbent material having an inner surface adapted to contact the skin of a user, and an outer surface, attachment tabs formed of a first type of filamentary attachment material extending from opposite sides of the diaper material at one end of the diaper and an elongated bar of a complementary type filamentary attachment material centrally located on the inner surface of the diaper material adjacent and parallel to an opposite end of the diaper, a folding method comprising the steps of:
   (a) front folding a portion of the diaper material carrying the bar onto the outer surface of the diaper material;
   (b) positioning the bar longitudinally on the diaper material to establish a proper length for the user; and
   (c) coupling the attachment tabs to the bar at proper positions to secure the diaper to the user.

17. The method of claim 16, including, between steps (b) and (c), the step of making an accordion fold in the diaper material beneath the bar to shorten the diaper to a newborn or premature infant size.

18. The method of claim 16, including, prior to step (a), the step of folding opposite side portions of the diaper onto the outer surface of the diaper material to establish a proper diaper width.

19. The method of claim 16, including, between steps (b) and (c), the step of folding opposite side portions of the diaper onto the inner surface of the diaper material to establish a proper diaper width.

20. An adjustable size diaper, comprising:
   an absorbent material having an inner surface adapted to contact the skin of a user when worn, and an outer surface;
   receiver loops positioned on the diaper material adjacent one end of the diaper;
   a belt positioning strip longitudinally extending along a central portion of the outer surface of the diaper material;
   a belt adapted to contact said positioning strip and extend through said loops; and
   means including filamentary attachment material for releasably securing the belt selectively to different longitudinal portions of said positioning strip wherein said receiver loops comprise a pair of receiver loops having portions secured to the diaper material and adapted to receive respectively, opposite ends of said belt, said belt releasably secured with respect to said diaper material only at said belt positioning strip.

21. The diaper of claim 20, wherein said positioning strip is stitched to the diaper material at a plurality of points along the strip to establish a plurality of longitudinally spaced-apart loops for receiving said belt.

22. The diaper of claim 20, wherein said positioning strip and said belt are provided with mutually complementary filamentary attachment material to enable the strip and belt to releasably couple to each other.

23. The diaper of claim 21, wherein said positioning strip and said belt are provided with mutually complementary filamentary attachment material to enable the strip and belt to releasably couple to each other.

24. The diaper of claim 20, wherein said receiver loops are positioned at opposite corners of the diaper material.

25. The diaper of claim 20, wherein said receiver loops are positioned adjacent and symmetrically about a longitudinal axis of the diaper.

26. The diaper of claim 1, wherein said diaper further includes a layer of water-impervious material.

27. A method of making a fabric diaper comprising:
   positioning a first strip of filamentary type attachment material on a surface of a moisture absorbent fabric parallel to and spaced apart from one end of the fabric, making a first stitch along only a portion of the full width of the fabric and against of said first strip to create a tuck in an outer surface of the fabric causing the first strip to tend to front fold onto the fabric;

positioning second strips of a complementary filamentary type attachment material at both corners of the opposite end of the fabric, the second strips extending inwardly from said corners;

folding at least portions of the edge of the fabric inward to establish a fold; and making a single stitch along substantially the entire fold to secure the second strips to the fabric while reinforcing the edge of the fabric.

28. The method of claim 27, including the additional steps of positioning third strips of said complementary filamentary attachment material on said second strips prior to the folding step, the third strips functioning as lint covers for said second strips.

29. The method of claim 27, including an additional step of inserting elastic strips within the folded edge of the fabric during said stitching step.

* * * * *